(12) United States Patent
Fortuna et al.

(10) Patent No.: US 10,624,594 B2
(45) Date of Patent: *Apr. 21, 2020

(54) RADIOLOGICAL IMAGING SYSTEM OCCUPYING A REDUCED SPACE

(71) Applicant: IMAGINALIS S.R.L., Florence (IT)

(72) Inventors: Damiano Fortuna, Rignano Sull'Arno (IT); Leonardo Manetti, Montevarchi (IT)

(73) Assignee: IMAGINALIS S.R.L., Florence (IT)

( * ) Notice: Subject to any disclaimer, the term of this patent is extended or adjusted under 35 U.S.C. 154(b) by 164 days.

This patent is subject to a terminal disclaimer.

(21) Appl. No.: 15/818,253

(22) Filed: Nov. 20, 2017

(65) Prior Publication Data
US 2018/0070900 A1    Mar. 15, 2018

Related U.S. Application Data

(63) Continuation of application No. 14/800,656, filed on Jul. 15, 2015, now Pat. No. 9,820,706.

(30) Foreign Application Priority Data

Jul. 16, 2014 (IT) .............................. MI2014A1296

(51) Int. Cl.
| H05G 1/02 | (2006.01) |
| A61B 6/00 | (2006.01) |
| A61B 6/04 | (2006.01) |
| A61B 6/03 | (2006.01) |
| A61B 6/10 | (2006.01) |

(52) U.S. Cl.
CPC ............ *A61B 6/4435* (2013.01); *A61B 6/035* (2013.01); *A61B 6/0407* (2013.01); *A61B 6/102* (2013.01); *A61B 6/4405* (2013.01)

(58) Field of Classification Search
CPC ........... A61B 6/00; A61B 6/04; A61B 6/4435; A61B 6/0407; A61B 6/4441; A61B 6/032; A61B 6/035; A61B 6/03; A61B 6/10; A61B 6/102; A61B 6/4405; H05G 1/02
USPC ............................. 378/195, 196, 209; 5/601
See application file for complete search history.

(56) References Cited

U.S. PATENT DOCUMENTS

| 7,300,205 B2 | 11/2007 | Grady |
| 9,820,706 B2 * | 11/2017 | Fortuna ................ A61B 6/4435 |

* cited by examiner

*Primary Examiner* — Jurie Yun

(74) *Attorney, Agent, or Firm* — Steptoe & Johnson LLP (57) ABSTRACT

A radiological imaging system including a bed extending along a main direction, and a load-bearing structure supporting the bed in a raised position. The system includes a collapsible gantry having a circular trajectory of expansion lying on a positioning plane, and the collapsible gantry includes a source to emit radiation and a detector to receive the radiation. The gantry also includes a casing housing the source and the detector. The casing includes a fixed arched module and a mobile arched module. There is a rotation mechanism suitable to rotate the collapsible gantry in relation to the bed and the load-bearing structure to vary the inclination of the positioning plane in relation to the main direction. There is also a kinematic expansion mechanism connected to the casing to translate the mobile arched module with respect to the fixed arched module.

10 Claims, 6 Drawing Sheets

RADIOLOGICAL IMAGING SYSTEM OCCUPYING A REDUCED SPACE

CROSS-REFERENCE TO RELATED APPLICATIONS

This application is a continuation of U.S. application Ser. No. 14/800,656, filed Jul. 15, 2015 which claims priority to Italian Application No. MI2014A001296, filed Jul. 16, 2014, which is herein incorporated by reference in its entirety.

FIELD

The present disclosure relates in general to the field of a radiological imaging system, and in particular, to a system and method for providing a radiological imaging system useful in the medical/veterinary sphere to obtain images of at least a portion of the internal anatomy of a patient and thus, perform analyses, diagnoses, or other assessments of the patients.

BACKGROUND

As is known, the radiological imaging devices currently available on the market have a standard structure including: a bed on which the patient is placed in order to perform image scanning of the patient and a gantry, which houses a source for emitting X-rays and a detector for receiving the X-rays.

Given the need to contain the source, the detector and the movement system, the gantry is cumbersome and, in particular, has a diameter of at least 1.5 meters and cannot therefore be maneuvered through doors or other passages present in a hospital. For that reason, if radiological imaging needs to be performed to verify the successful outcome of an operation, the patient must be lifted from the operating table, placed on a bed, moved to another part of the hospital to the room where the imaging device is installed, lifted again and then placed on the bed of the radiological imaging device. This procedure may be further complicated if the radiological imaging reveals the need for further surgery, in which case, the patient would need to be taken back to the operating room. Additionally, such maneuvers often entail problems for the patient and therefore need to be performed with particular care and expertise. Consequently, the length of time needed to perform the aforementioned maneuvers increases.

SUMMARY

Existing limitations associated with the foregoing, as well as other limitations, can be overcome by a method for operating a radiological imaging device, and by a system, apparatus, and computer program that operates in accordance with the method. Briefly, and in general terms, the present disclosure is directed to various embodiments of a radiological imaging system.

A radiological imaging system with a bed, a collapsible gantry, and the method of operating thereof are disclosed. In one embodiment, the radiological imaging system permits the patient to be maneuvered easily and reduces risks to the patient. Also, the system may permit a reduction in the maneuvers involving the patient. The radiological imaging system may further permit different analyses/operations to be performed on the patient conveniently and quickly.

According to one embodiment, a radiological imaging system, includes a bed extending along a main direction, and a load-bearing structure suitable to support the bed in a raised position. A free chamber is defined between the load-bearing structure and the bed. The system also includes a gantry having a circular trajectory of expansion lying on a positioning plane, and the gantry has a source for emitting radiation and a detector for receiving the radiation. The gantry includes a casing to house the source and the detector. The casing includes a fixed arched module and a first mobile arched module. There is also a rotation mechanism connected to the gantry to rotate the gantry in relation to the bed and to the load-bearing structure to vary the inclination of the positioning plane in relation to the main direction. As discussed below, in one embodiment, the rotational mechanism connected to the gantry may be disposed within the free chamber and attached to the load-bearing structure. There also is at least one kinematic expansion mechanism connected to the casing of the gantry. The kinematic expansion mechanism is able to translate the first mobile arched module with respect to the fixed arched module of the casing. The movement of the first mobile arched module varies the angular extension of the casing and the gantry.

In one embodiment of the radiological imaging system, the at least one kinematic expansion mechanism translates the first mobile arched module along the circular trajectory of expansion.

The radiological imaging system may include a rest configuration in which the positioning plane is substantially parallel to the main direction and wherein the first mobile arched module is substantially overlapped with the fixed arched module. In this configuration, the angular extension of the casing is substantially equal to the angular extension of the fixed arched module. In addition, the radiological imaging system may include a first working configuration wherein the positioning plane is substantially perpendicular to the main direction, and wherein the first mobile arched module at least partially protrudes from the fixed arched module. When the first mobile arched module at least partially protrudes from the fixed arched module, the angular extension of the casing is higher than the angular extension of the fixed arched module.

In the rest configuration, the gantry is at least partially housed in the free chamber. In one embodiment, the gantry is completely collapsed within the free chamber. Also, in the first working configuration, the positioning plane of the gantry may be substantially perpendicular to the main direction.

In one embodiment, the casing of gantry includes a first mobile arched module disposed in a first end of the fixed arched module and a second mobile arched module disposed in a second end of the fixed arched module. In this embodiment, the least one kinematic expansion mechanism is able to move the first and second mobile arched modules in opposite directions. In one embodiment, the least one kinematic expansion mechanism is adapted to independently move the first and second mobile arched modules. It has also been contemplated that the first and second mobile arched modules may be manually moved with respect to the fixed arched module.

Furthermore, the system may include a second working configuration wherein the positioning plane of the gantry is substantially perpendicular to the main direction and the ends the first and second mobile arched modules reach a mutual contact point and angle of extension of the casing and the gantry is about 360°. All angles describe herein may vary by up to ten percent.

In one embodiment of the radiological imaging system, the first and second mobile arched modules may have an angular extension, calculated along the circular trajectory of expansion, substantially equal to 90° and the fixed arched module may have an angular extension between about 180° and about 210°. All angles describe herein may vary by up to ten percent.

In yet another embodiment, the radiological imaging system may include a first cover block disposed in one end of the fixed arched module at least when the radiological imaging system is in the rest configuration. A second cover block may be disposed in another end of the fixed arched module when the system is in the rest configuration.

Other features and advantages will become apparent from the following detailed description, taken in conjunction with the accompanying drawings, which illustrate by way of example, the features of the various embodiments.

BRIEF DESCRIPTION OF THE DRAWING

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Each of the features and teachings disclosed herein can be utilized separately or in conjunction with other features and teachings to provide a radiological imaging system occupying a reduced space. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that each of these specific details are not required to practice the teachings of the present disclosure.

Moreover, the various features of the representative examples may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples. In this document, measurements, values, shapes, angles, and geometric references (such as perpendicularity and parallelism), when associated with words like "about" or other similar terms such as "approximately" or "substantially," should be construed to allow for measurement errors or others errors due to production and/or manufacture process, and may vary by up to ten percent.

With reference to FIGS. 1a-5, reference numeral 1 denotes the radiological imaging system.

The radiological imaging system 1 is useful in both the medical and veterinary applications for performing radiological imaging of at least one portion of the internal anatomy of a patient. In particular, the radiological imaging system 1 is useful for performing X-rays, CT scans, fluoroscopy and other radiological imaging examinations.

In one embodiment, the radiological imaging system 1 includes a control unit 1a (shown in FIG. 1e) suitable to control the functioning of the radiological imaging system 1. The system also includes a bed 20 extending along a main direction (or main axis of extension) 20a and having a support surface 20b to support the patient. The system includes a gantry 30 suitable to perform the radiological imaging of at least a portion of the patient and defining a main axis of expansion 30a. The gantry may have a circular trajectory of expansion 30b, in a positioning plane 30c having, appropriately, its center on the axis of expansion 30a. The system also may include a load-bearing structure 40 suitable to support the gantry 30 and, in a raised position, the bed 20 and defining a free chamber 40a. The gantry in this embodiment is a collapsible gantry.

Figure 1A:
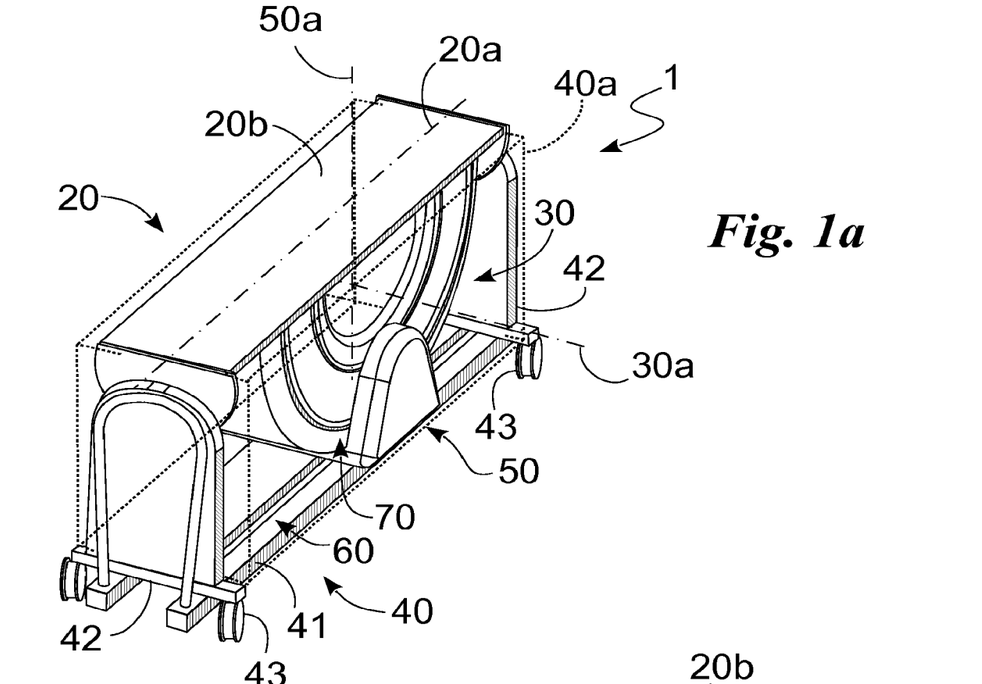
FIGS. 1a-1e show, in perspective, an exemplary radiological imaging system in a possible operating sequences.
Figure 1B:
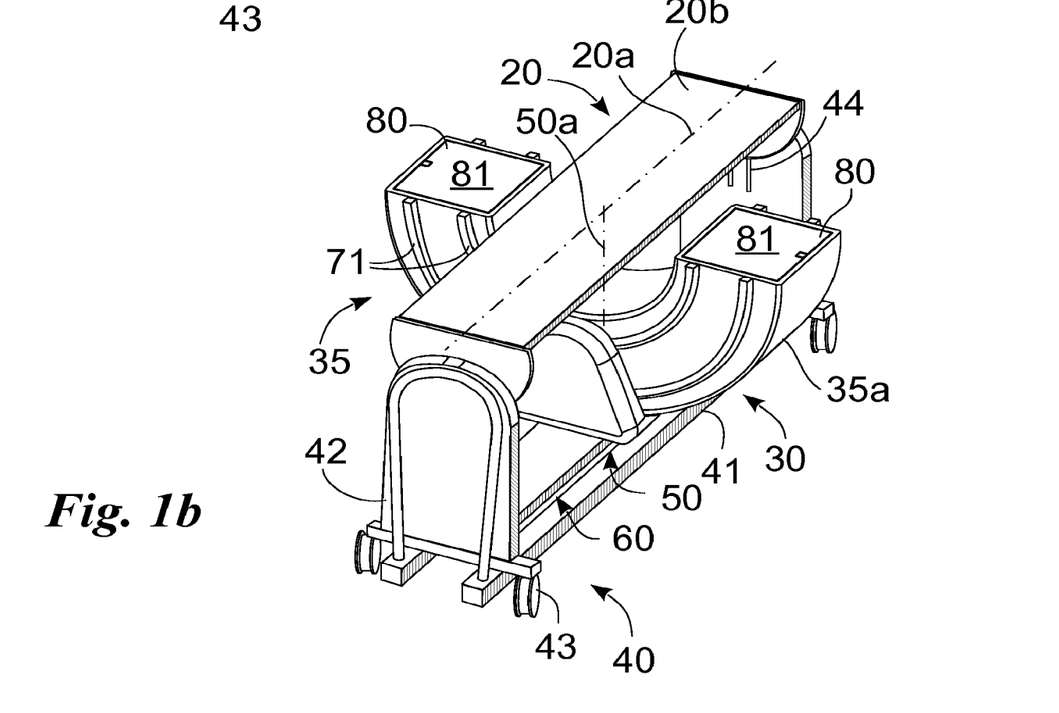
Figure 1C:
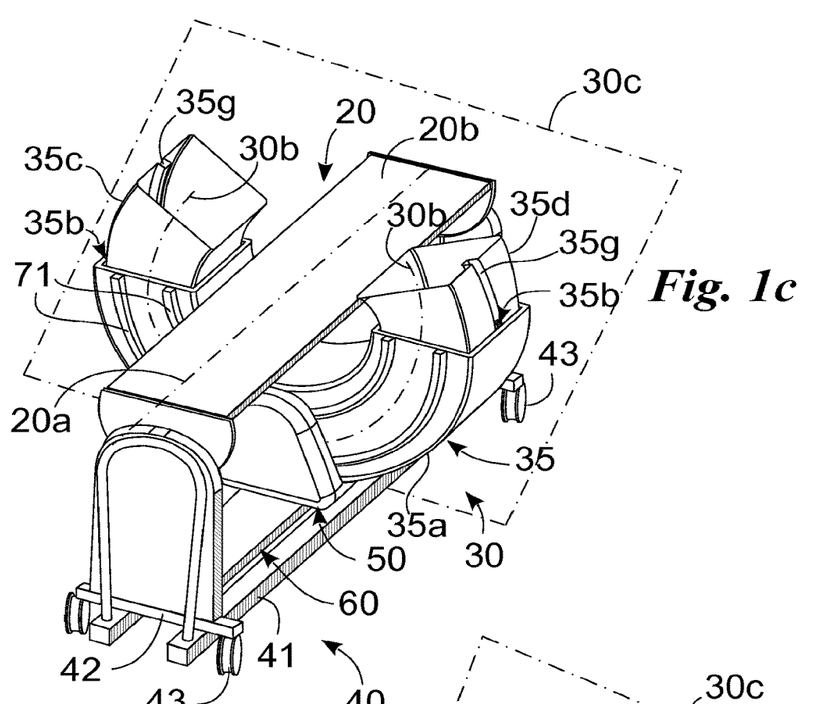

As best shown in FIGS. 1a-1c, the bed 20 extends along a main direction (or main axis of extension) 20a substantially parallel and, in particular, coinciding with the main axis of expansion 30a. The supporting surface 20b may be substantially parallel to the main axis of expansion 30a and, in particular, arranged to lie almost parallel to the support surface of the radiological imaging system 1.

Figure 1D:
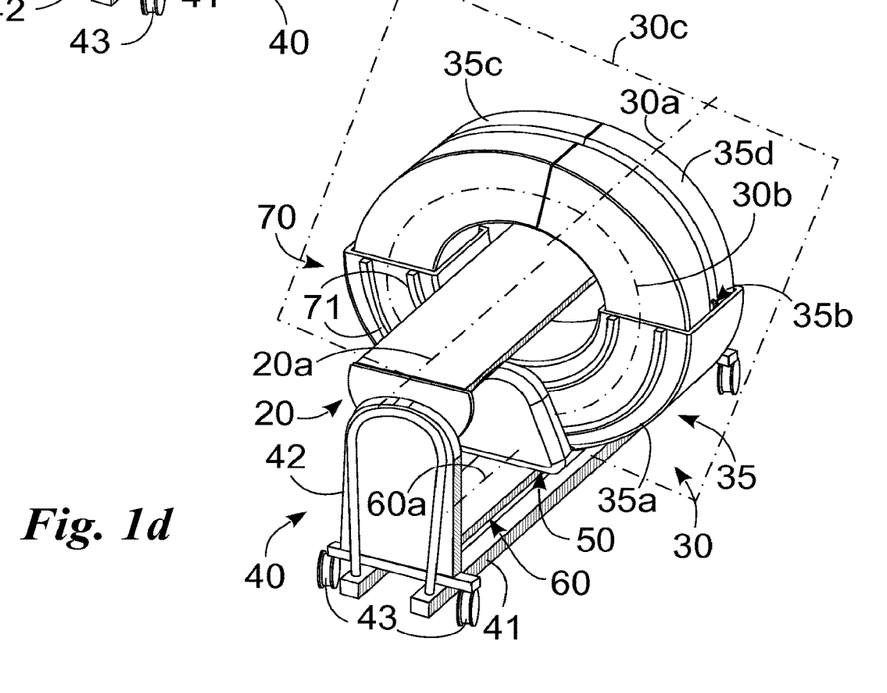
Figure 1E:
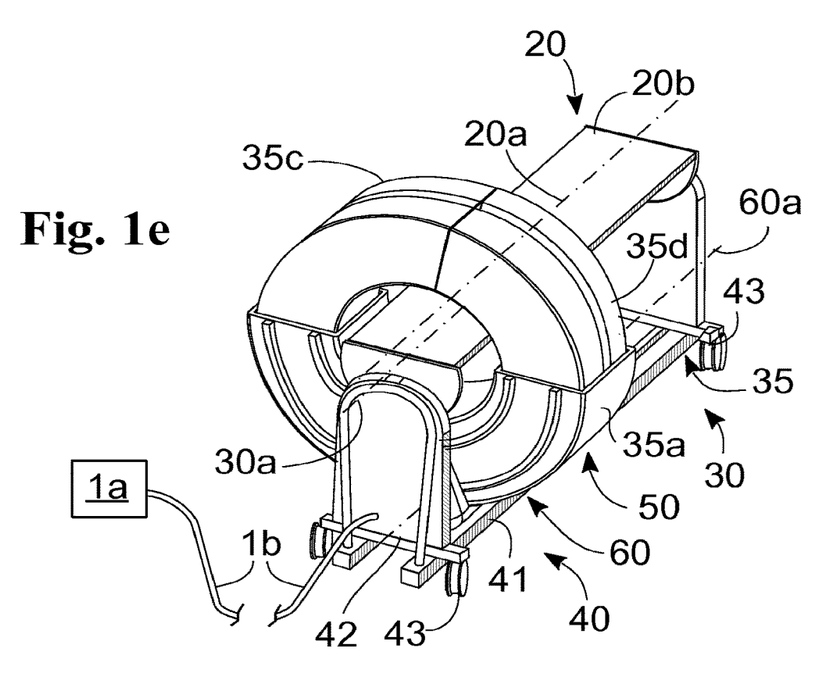

In one embodiment, the control unit 1a may be connected to the other components of the system 1 by wireless connection and/or by a cable 1b as shown in FIG. 1e. The control unit 1a may control and command the radiological imaging system 1. More specifically, the control unit 1a may control the gantry 30 and its movements. The control unit 1a may include a command board able to automatically control and command the radiological imaging system 1 and any interface components (e.g., touch screen, keyboard, joystick, etc.) suitable to allow the operator to command the radiological imaging system.

As shown in the examples of FIG. 1, the load-bearing structure 40 includes a base 41 that comes in contact with the floor and is suitable to support the gantry 30. Also in this example is at least one column 42 suitable to support the bed 20 in the raised position with respect to the base 41. There may be two columns 42 to support the bed. However, additional columns may be included to support the weight of the bed and the patient. In one embodiment, the system includes movement wheels 43, preferably pivoting, suitable to be arranged between a floor surface upon which the system 1 is disposed and the base 41 to allow the movement of the system 1 and at least one actuator 44 suitable to move the bed 20 with respect to the base 41. Multiple actuators may be used to move the bed.

As shown in the exemplar figures, the base 41 and the at least one column 42 limit and define the chamber 40a. In detail the chamber 40a is delimited at the bottom (closed to the floor) by the base 41; along a side face by the column 42; if present, along a second side face opposite to the first by the second column 42; and, optionally, the top by the bed 20.

The actuators 44 are arranged between the bed 20 and each column 42 to modify the extension of the chamber 40a via a translational movement substantially perpendicular to the main direction (or axis of extension) 20a. Alternatively, the actuators 44 modify the internal chamber 40a through a rotational movement of the bed 20 about an axis substantially parallel to the main direction 20a.

Arranged between the base 41 and the gantry 30, the radiological imaging system 1 includes a rotation mechanism 50 suitable to rotate the gantry 30 about an axis of rotation 50a in one embodiment. The system may also include a translation mechanism 60 suitable to move the gantry 30 along an axis of translation 60a substantially parallel to the main direction 20a (FIG. 1e).

The translation mechanism 60 is arranged between the base 41 and the gantry 30 and includes a linear guide 61. The linear guide 61 may be motorized and suitable to control the translation along the axis of translation 60a. The translation mechanism may also allow the translation along the axis of translation to be done manually. In this example, the translation mechanism 60 includes a carriage 62 connected to the gantry 30 to slide along the linear guide 61 thus translating the gantry 30.

By way of example, the rotation mechanism 50 is arranged between the translation mechanism 60 and the gantry 30 and suitable to rotate the gantry 30 with respect to an axis of rotation 50a substantially transverse and, in particular, substantially perpendicular to the main axis of extension 20a.

In one embodiment, the rotation mechanism 50 includes a fixed plate 51 suitable to be connected to the carriage 62, and a mobile plate 52 connected to the gantry 30. In this embodiment, the rotational mechanism 50 may also include pins, bearings or other similar elements defining the axis of rotation 50a. A control lever 53 suitable to be held by the operator may permit the operator to manually control the rotation, about the axis of rotation 50a, of the mobile plate 52 and, thus, of the gantry 30 with respect to the fixed plate 51. As an alternative to the control lever 53, the rotation mechanism 50 can include a motor suitable to control the rotation of the gantry 30.

In one example, the control lever 53 is suitable to be connected to holes provided in the plates 51 and 52 so as to define, for the gantry 30, a first rotational blocked position in which the main direction (or axis of expansion) 30a, is substantially parallel to the main direction (or axis of extension) 20a, and the circular trajectory of expansion 30b and the positioning plane 30c are substantially perpendicular to the main direction 20a. A second rotational blocked position in which the main axis of expansion 30a is substantially perpendicular to the main direction 20a, the circular trajectory of expansion 30b, and the positioning plane 30c are substantially parallel to the main direction 20a. In another example, the lever 53 may additionally define a third rotational blocked position in which the main axis of expansion 30a is substantially parallel to the axis of extension 20a, and the circular trajectory of expansion 30b and the positioning plane 30 are substantially perpendicular to the main direction 20a, but the gantry 30 is rotated by 180° with respect to the first position.

By way of example only, and not by way of limitation, the gantry 30, rotatable by virtue of the rotation mechanism 50, includes a source 31 suitable to emit radiation, such as X-rays, and defining a central axis of propagation 31a preferably substantially perpendicular to the main directions 20a and 30a. The gantry also includes a detector 32 suitable to receive the radiation after it has traversed the patient's body and the bed 20. There may also be at least one internal mover able to rotate the source 31 and the detector 32 around the main direction (axis of expansion) 30a defining, for the detector 32, an inner sliding trajectory 33a and, for the source 31, an outer sliding trajectory 34a distinct from the inner trajectory 33a. In one embodiment, the gantry also includes a casing 35 suitable to house the source 31, the detector 32, and the movers. In one example, the source, detector, and movers are located within the casing of the gantry regardless of the configuration of the system.

The radiological imaging system 1 is useful in both the medical and veterinary applications for performing radiological imaging of at least one portion of the internal anatomy of a patient. In particular, the radiological imaging system 1 is suitable for performing X-rays, CT scans, fluoroscopy and other radiological imaging examinations. Thus, in one embodiment, the detector 32 may have a first sensor 32a, suitable to selectively carry out tomography or fluoroscopy and defining a first sensitive surface 32b suitable to detect the radiation. A second sensor 32c may be suitable to perform X-rays and define a second sensitive surface 32d suitable to detect the radiation. In one embodiment, the detector may include a movement apparatus suitable to move the first sensor 32a and the second sensor 32c in relation to the source 31. It has been contemplated other arrangements of various sensors of the detector can be used, the embodiment described is merely one example.

By way of example only, and not by way of limitation, the first sensor 32a may include a flat panel, while the second sensor 32c may include at least one linear sensor. In another example, the first sensor 32a includes two linear sensors, positioned alongside each other and defining substantially coplanar second sensitive surfaces 32d. Alternatively, the second sensor 32c may include one or more rectangular sensors or other sensors. In other embodiments, other types of sensors can be used for sensors 32a and 32c and the second sensor 32c may include more or less than two sensors. It has also been contemplated that the second sensor 32c may include one or more rectangular sensors or other sensors.

In yet another embodiment, the detector 32 may envisage a third sensor, not shown in the drawing, preferably consisting of a direct photonic counting sensor.

The movement apparatus is suitable to move the sensors 32a and 32c in relation to the source 31 defining a first active configuration wherein only the first sensor 32a is able to receive the radiation emitted by the source 31 and a second active configuration wherein only the second sensor 32c is able to receive the radiation.

In one embodiment, the movement device moves the detectors 32a and 32c in such a way that, in each of the active configurations the sensitive surfaces 32b and 32d are substantially perpendicular to the axis of propagation 31a so that the distance of the source 31 from the detectors 32a and 32c, and more specifically, from the surfaces 32b and 32d is kept unvaried.

Furthermore, in the embodiment in which the detector 32 envisages the third sensor, the movement apparatus moves the three sensors, in the same way as described below, defining a third active configuration wherein only the third sensor is able to receive the radiation emitted by the source 31. In this embodiment, the sensitive surface of the third sensor is substantially perpendicular to the central axis of propagation 31a. The distance of the source 31 from the third sensor and more specifically from its sensitive surface is equal to that defined by the source 31 and by the other surfaces 32b and 32d in the other active configurations.

Figure 4A:
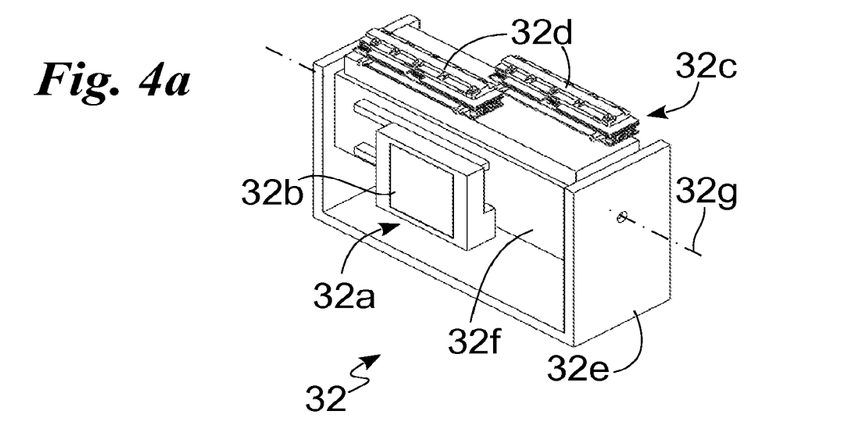
FIGS. 4a and 4b show an embodiment of a subassembly of the system.
Figure 4B:
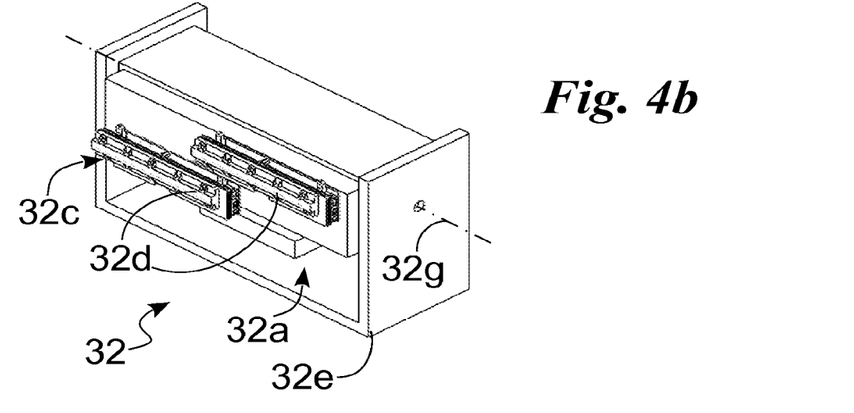
Figure 5:
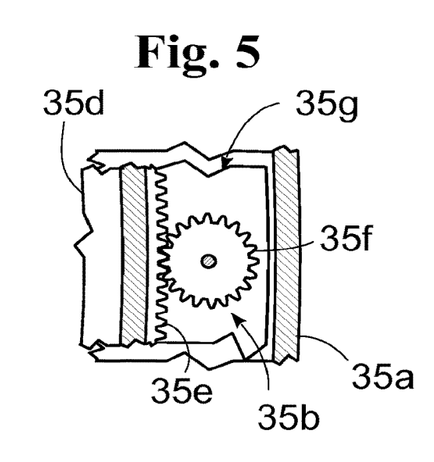
FIG. 5 shows another subassembly of the system.

As shown in FIGS. 4a and 4b, the movement apparatus may include a load-bearing body 32e suitable to support the detectors 32a and 32c and a motor 32f. The motor may be an electric motor, or any type of motor suitable to rotate the detectors 32a and 32c along an axis of rotation 32g. In one embodiment the detectors 32a and 32c are rotated substantially perpendicular to the axis of propagation 31a. The detectors 32a and 32c may be rotated substantially parallel to or perpendicular to the main direction 20a.

In one example, the amplitude of rotation of the detectors 32a and 32c is substantially equal to 90° or to 180° so that, in the first active configuration (FIG. 4a), the first surface 32b is substantially perpendicular to the central axis of propagation 31a, and the second surface 32d is substantially parallel to the central axis of propagation 31a. In the second active configuration (FIG. 4b), the first surface 32b may be substantially parallel to the central axis of propagation 31a, and the second surface 32d may be substantially perpendicular to the central axis 31a. In this embodiment, the distance from the source 31 is the same as that between the source and the first surface 32b in the previous configuration.

In the embodiments shown, the casing 35 forms the outer body of the gantry 30 and, therefore, it defines the dimensions and, in particular, the angular extension of the gantry 30.

By way of example, the casing 35 and, therefore, the gantry 30 may be telescopic to vary in extension along the circular trajectory of expansion 30b. The telescopic casing defines, for the radiological imaging system 1, at least one rest configuration and at least one working configuration. The system may have multiple rest configurations and working configurations that may vary by degree.

In one example of the rest configuration (FIGS. 1a and 2a), the casing 35 and the gantry 30 are contracted and have minimal angular dimensions. Therefore, in this rest configuration, the casing 35, the gantry 30, and the positioning plane 30c, define an arc of a circumference substantially centered on the main direction (axis of expansion) 30a and having an angular extension of, for example, approximately less than 270°. In one embodiment, the arc of a circumference has an angular extension of approximately less than 240° and, in another embodiment, less than about 210° and, in yet another embodiment, approximately equal to about 190°.

Furthermore, in the rest configuration, the gantry 30 and the trajectory of expansion 30b define a positioning plane 30c substantially parallel to the main direction 20a. In one embodiment, the gantry 30 is housed in the free chamber 40a thereby reducing the overall dimensions of the device 1 to a minimum and, as a consequence, leaving the support surface 20b substantially clear and easily accessible from any point. In one embodiment, the gantry 30 is entirely housed in the free chamber 40a when in the rest configuration, and in another embodiment, the gantry 30 is at least partially housed in the free chamber 40a when in the rest configuration.

As an example, in the at least one working configuration, as shown in FIGS. 1c-1e and 2c, the casing 35 and the gantry 30 have an angular extension greater than that of the rest configuration to at least partially surround a portion of the bed 20 and of the patient on the bed 20. Additionally, the casing 35 and the gantry 30, are rotated with respect to the rest configuration using the rotation mechanism 50, in order to place the positioning plane 30c substantially transverse to the main direction (or axis) 20a. In this example, the casing 35 and the gantry 30 are rotated, with respect to the rest configuration, of an angle of approximately 90° and the plane 30c is almost perpendicular to the main direction 20a and the axis 30a is approximately parallel to the main direction 20a.

In addition to the above exemplary configurations, the radiological imaging system 1 may also define at least one supplementary working configuration in which the casing 35 and the gantry 30 have an angular extension substantially analogous to that of the aforementioned working configuration and the positioning plane 30c is substantially perpendicular to the main direction 20a, but rotated by approximately 180°, around the axis of rotation 50a, with respect to the working configuration so that the gantry 30 faces an opposite direction from the working configuration.

In one embodiment, the radiological imaging system 1 defines another working configuration of maximum extension (FIGS. 1d-1e and 2c) and, additionally, a supplementary working configuration of maximum extension in which the casing 35 and the gantry 30 are substantially closed. In this embodiment, the casing 35 and the gantry 30 have an angular extension and an expansion trajectory circular 30b of substantially 360°.

In certain embodiments, the casing 35 includes at least two modules having a preferred trajectory of extension that substantially coincides with the circular trajectory 30b and having cross-sections of different extensions to enable a reciprocal insertion.

In one embodiment, the casing 35 includes a fixed arched module 35a suitable to be connected to the rotation mechanism 50. The casing 35 also includes at least one mobile arched module having a lesser cross-section than the fixed module 35a to be housed therein. In one embodiment, the casing 35 includes two mobile arched modules, and these two mobile arched modules may be housed within the fixed module 35a. There may also be at least one kinematic expansion mechanism 35b suitable to move the at least one mobile arched module with respect to the fixed module 35a along the circular trajectory of expansion 30b to allow the casing 35 to assume any angular extension between 360° and the angular extension of the fixed arched module 35a.

By way of example, the casing 35 may include a fixed arched module 35a, a first mobile arched module 35c disposed at an end of the fixed module 35a, a second mobile arched module 35d disposed at the opposite end of the fixed arched module 35a. The first and second mobile arched modules may be substantially symmetrical. In this example, the system may include a kinematic expansion mechanism 35b able to move, independently from each other, the first and second mobile arched modules 35c and 35d with respect to the fixed module 35a along the trajectory of circular expansion 30b. The movement of the first mobile arched module 35c is in the opposite direction of the second mobile arched module 35d so that at maximum extension, the first and seconds mobile arched modules 35c and 35d reach a mutual contact point.

In one embodiment, the fixed module 35a and mobile arched modules 35c and 35d have substantially the same expansion axis almost coinciding with the trajectory of circular expansion 30b.

The first and second mobile arched modules 35c and 35d may have a cross-section different from that of the fixed module 35a to at least partially overlap the fixed module 35a. In another embodiment, the cross-section of the mobile arched modules is the same as the cross-section of the fixed module. In one example, the mobile modules 35c and 35d may have a cross-section smaller than that of the fixed arched module 35a to be housed inside the fixed arched module.

In one embodiment, the kinematic expansion mechanism 35b is adapted to move the mobile arched modules 35c and 35d with respect to the fixed module 35a to vary the extension of the portion of each mobile arched module superimposed and, in particular, included in the fixed arched module 35a.

In one example, the kinematic expansion mechanism 35b is adapted to arrange, in the rest configuration (FIGS. 1a and 2a), each mobile arched module 35c and/or 35d totally located inside in the fixed module 35a so that the angular extent of the gantry 30 is substantially equal to that of the fixed module 35a. In the rest configuration of this example, the mobile arched modules 35c and 35d are totally inside the fixed module 35a of the casing 35 and may be substantially in contact with each other.

In one embodiment, in the at least one working configuration (FIGS. 1d and 2c) and, if provided, in the at least one supplementary working configuration, the kinematic expansion mechanism 35b may allow each of the mobile arched modules 35c and 35d to protrude from the fixed module 35a so that the angular extent of the gantry 30 is greater than the one of the fixed module 35a and, almost equal to that of the fixed module 35a plus the angular extent of the portion of each mobile module 35c and 35d protruding from the fixed module 35a.

In one embodiment, the kinematic mechanism 35b (FIG. 5) is mechanical and, for example, includes at least one rack 35e disposed on each mobile arched module 35c and 35d and extending along the circular trajectory of expansion 30b. The kinematic mechanism 35b may also include at least one motorized toothed wheel 35f hinged to the fixed arched module 35a, engaging with the racks 35e to control the motion of the mobile arched modules 35c and 35d along the trajectory 30b.

Alternatively, the kinematic mechanism 35b may move each mobile arched module 35c and 35d with respect to the fixed arched module 35a through belts, arched actuators, or, in a further alternative, it can be of magnetic type. In a separate embodiment, the mobile arched modules 35c and 35d are manually moved with respect to the fixed arched module 35a. There may be no kinematic mechanism 35b in this specific embodiment.

In order to store the kinematic expansion mechanism 35b between the modules 35a, 35c and 35d, each mobile arched module 35c and 35d is provided with a recess defining a housing channel 35g for the kinematic expansion mechanism 35b.

In one embodiment, the source 31 and the detector 32 and the one or more internal movers may have an angular extension below the angular extension of the fixed module 35a.

In an exemplary embodiment, in order to move the source 31 and the detector 32 in an independent manner, the gantry 30 includes an internal inner mover 33 defining, for the detector 32, an inner sliding trajectory 33a and an internal outer mover 34 defining, for the source 31, an outer sliding trajectory 34a distinct from the outer sliding trajectory 33a.

The inner and outer sliding trajectories 33a and 34a may have a circular shape with its center on the axis 30a to move the source 31 and/or the detector 32 without substantially changing its distance from the main axis of expansion 30a. In one example, the inner and outer sliding trajectories 33a and 34a lie on a single plane substantially perpendicular to the main axis of expansion 30a and substantially parallel to the positioning plane 30c.

In one exemplary embodiment, the outer sliding trajectory 34a defines a distance from the source 31 to the main axis of expansion 30a, and the inner sliding trajectory 33a defines a distance of the detector 32, i.e. the sensitive surfaces 32b or 32d, from the main axis of expansion 30a. The radius defined by the outer sliding trajectory 34a is greater than the radius defined by the inner sliding trajectory. It has been contemplated that the outer sliding trajectory 34a defines a distance of the source 31 from the main axis of expansion 30a between about 1100 mm and about 300 mm. This distance may also be between about 900 mm and about 480 mm. In this example, the inner sliding trajectory 33a defines a distance of the sensitive surface of the detector 32 from the main axis of expansion 30a between about 900 mm and about 150 mm and, in detail, between about 600 mm and about 300 mm.

By way of example only, each internal mover 33 and 34 may include an arched guide and at least one cart adapted to move it along the arched guide.

Figure 3A:
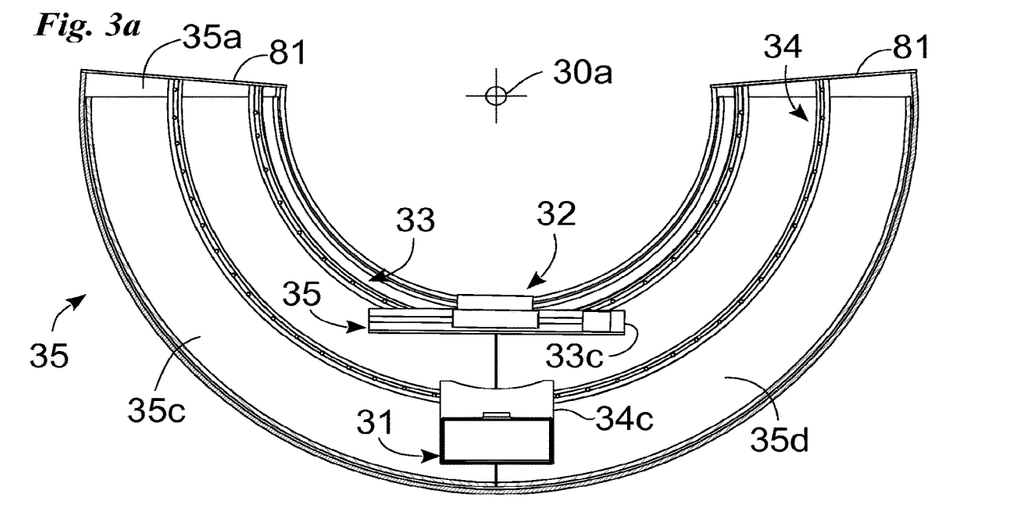
FIGS. 3a and 3b shows one embodiment of an assembly of the radiological imaging system.
Figure 3B:
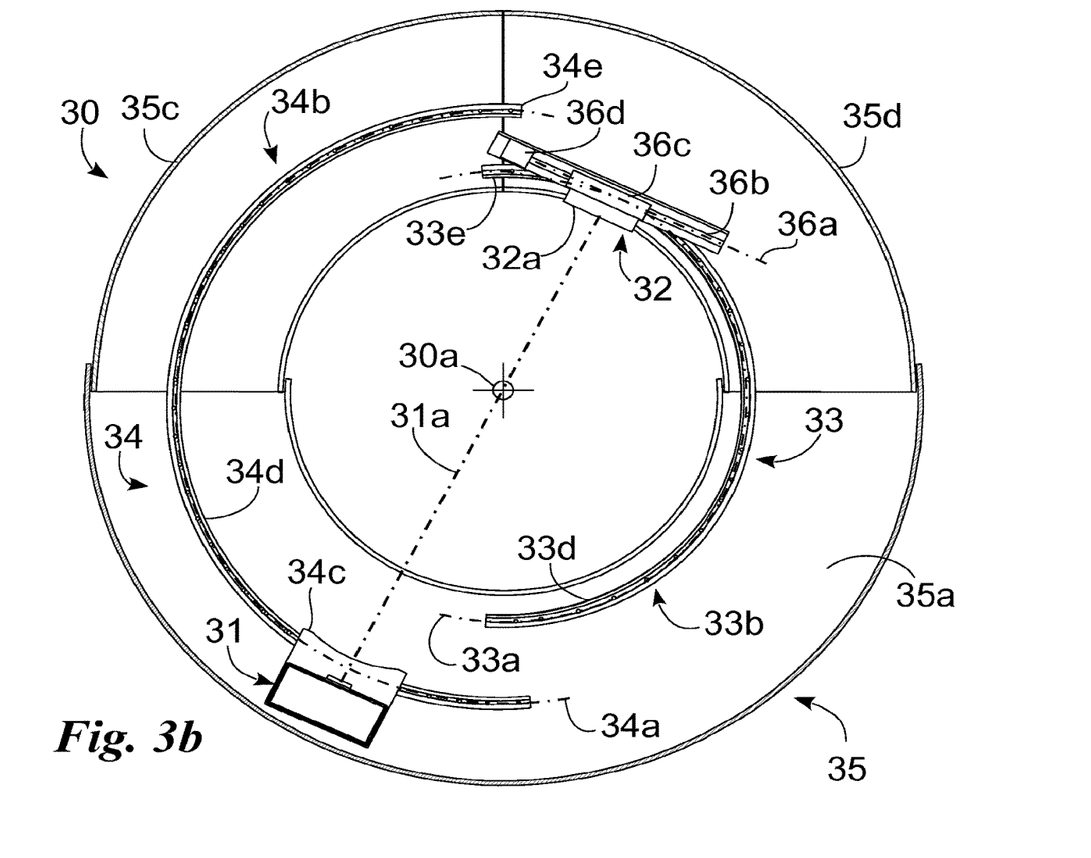

In one embodiment, best shown in FIGS. 3a and 3b, the internal inner guide 33 includes an inner arched guide 33b integral with the first mobile module 35c and defining the sliding trajectory 33a. The internal inner guide 33 also may include at least one inner cart 33c. The inner cart 33c may be motorized (electric) and preferably of recirculating ball type, although any suitable motor may be used. In this embodiment, the inner cart 33c may be constrained to the detector 32 and adapted to move it along the inner arched guide 33b and, therefore, along the inner trajectory 33a. The internal outer guide 34 may include an arched outer guide 34b integral with the second mobile arched module 35d and defining the sliding trajectory 34a. The internal outer guide 34 also may include at least one outer cart 34c. As with the inner cart 33c, the outer cart 34c may be motorized (electric) and preferably of recirculating ball type, although any suitable motor may be used. In this embodiment, the outer cart 34c may be constrained to the source 31 and adapted to move it along the outer arched guide 34b and, therefore, along the outer trajectory 34a.

In certain embodiments, an opening or slot may be disposed on each mobile arched module 35c and 35d, duplicating the guides 33b and 34b. Also in certain embodiments, a rack can be disposed on the arched guide 33b and 34b, on the side opposite to the inner and outer carts 33c and 34c. Further, the toothed wheel of the kinematic mechanism 35b may engage, through the opening or slot, the rack to control the motion of the mobile arched modules 35c and 35d by acting on the curved guide 33b and 34b.

In one embodiment, each arched guide 33b and 34b has an angular extension at least equal to 180° so that the internal movers 33 and 34 are able to rotate the detector 32 and source 31, respectively, by an angle between about 0° and about 180°. It has been contemplated that the arched guides 33b and 34b have an angular extension between about 180° and about 210°. In another embodiment, the arched guides 33b and 34b have an angular extension between about 190° and about 200°.

By way of example only, the inner arched guide 33b may be jointly bound to the first mobile arched module 35c so as to define, on opposite sides of and with respect to the first module 35c, a first inner protruding portion 33d and a second inner protruding portion 33e. In the rest configuration (FIG. 3a), the first inner portion 33d may be superimposed to the second mobile module 35d and the second inner protruding portion 33e may be cantilevered with respect to the mobile arched modules 35c and 35d. Also, in the working configuration of maximum extension (FIG. 3b), the first inner protruding portion 33d may be cantilevered with respect to the mobile arched modules 35c and 35d and the second inner protruding portion 33e may be superimposed to the second mobile arched module 35.

In one example, the outer arched guide 34b is jointly bound to the second mobile module 35d to define, on opposite sides of and with respect to the module 35d, a first outer protruding portion 34d and a second outer protruding portion 34e. In the rest configuration (FIG. 3a) of this example, the first outer portion 34d may be superimposed to the first mobile module 35c and the second outer protruding portion 34e may be cantilevered with respect to the mobile arched modules 35c and 35d. Also, in the working configuration of maximum extension (FIG. 3b), the first outer protruding portion 34d may be cantilevered with respect to the mobile arched modules 35c and 35d and the second outer protruding portion 34e may be superimposed to the first mobile module 35c.

In one embodiment, the first protruding portions 33d and 34d and the second protruding portions 33e and 34e respectively may have an angular extension equal to about 90° and about 10° to about 20°.

In certain embodiments, the internal movers 33 and 34 may move, the source 31 and the detector 32 with the guides 33b and 34b along the trajectories 33a and 34a by an angle between about 0° and about 180° or at least about 360°, with respect to the mobile arched modules 35c and 35d. Therefore, each mover 33 and 34 may include a control group adapted to move, along the sliding trajectory 33a and 34a, the arched guide 33b and 34b relative to the casing 35 and, the mobile modules 35c and 35d.

In one embodiment, the control group defines for each internal mover 33 and 34 a contracted condition, in which the inner arched guide 33b and the outer arched guide 34b are respectively substantially superimposed to the first mobile module 35c and to the second module 35d, and an expanded condition in which the arched guide 33b and 34b protrudes at least partially from the corresponding mobile module 35c and 35d.

In one embodiment, the control group is adapted to move the arched guide 33b or 34b by way of a magnetic field and it includes a magnet, fixed on the mobile module 35c and/or 35d, suitable to control the arched guide 33b or 34b interacting with permanent magnets connected to the arched guide 33b or 34b. Alternatively, the control group is adapted to mechanically move the arched guide 33b or 34b and it may include a motorized toothed wheel hinged, preferably, to the arched guide 33b or 34b and suitable to engage with a rack obtained on the mobile arched module 35c and/or 35d.

In this embodiment, the arched guide 33b and 34b may have angular extension almost between 90° and 110°.

In certain embodiments, the internal movers 33 and 34 can be of telescopic type and, therefore, able to move, of an angle between about 0° and about 180°, the source and detector by a variation of their angular extension along the trajectory 33a and 34a. Therefore, each mover 33 and 34 may include an additional arched guide extending almost along the trajectory 30b and interposed between the arched guide 33b or 34b and the cart 33c or 34c to allow the cart 33c and 34c to slide on the additional arched guide. The control group may be adapted to vary the extension of the internal mover 33 or 34, along the sliding trajectory 33a and 34a, by moving one of the additional arched guides relative to the corresponding arched guide 33b and 34b and, therefore, to the casing 35.

In this embodiment, the control group of each guide 33 and 34 defines a contracted condition, in which the additional arched guide is substantially overlapping the corresponding arched guide 33b or 34b and mobile module 35c or 35d, and an expanded condition in which the additional arched guide protrudes at least partially from the corresponding arched guide 33b or 34b and mobile module 35c or 35d.

Additionally, the control group defines an internal mover 33 and/or 34 provided with a stroke-multiplying mechanism obtaining an output speed of greater amplitude, preferably of twice the amplitude, with respect to the input speed. Therefore, the control group includes a rack obtained on the mobile arched module 35c and/or 35d or 34b. The control group may also include an additional rack obtained on the arched guide 33b or 34b, and a motorized toothed wheel hinged to the additional arched guide. The motorized toothed wheel may be suitable to engage with both racks determining a speed of the additional guide (output speed) having an amplitude twice the amplitude of the input speed of the toothed wheel.

In this embodiment, each of the arched guides 33b and 34b and the additional guide have substantially the same angular extension, which may be between about 90° and about 110°.

In certain embodiments, inside the casing 35, the gantry 30 includes a sensor movement system 36 located between the detector 32 and the cart 33c of the internal inner guide 33 and able to translate the detector 32 keeping sensitive surfaces 32b and/or 32d almost perpendicular to the axis of propagation 31a.

In one embodiment, the sensor movement system 36 is adapted to translate the detector 32 along a flagging axis 36a substantially perpendicular to the axis of propagation 31a and, to the main axis of expansion 30a. In one embodiment, the sensor movement system 36 is adapted to translate the detector 32, with respect to a position in which the axis of propagation 31a intersect the center of the sensitive surfaces 32b or 32d, of a quantity between about ±400 mm and about ±50 mm, or substantially within about ±400 mm and about ±300 mm.

The sensor movement system 36 may include a flapping guide 36b defining the flapping axis 36a, a flapping cursor 36c supporting the detector 32 and able to slide along the flapping guide 36b, and a flapping motor 36d. The flapping motor 36d may be an electric motor, suitable to command the motion of the flapping cursor 36c along the flapping guide 36b.

In yet another embodiment, the imaging radiological imaging system 1 appropriately includes a compensating member 70 arranged between the gantry 30 and the rotation mechanism 60 and suitable to rotate the gantry 30 to facilitate the complete rotation of the source 31 and of the detector 32 about the bed 20 and, thus, about the patient. It has also been contemplated that the system includes one or more integral or removably attached cover blocks 80, preferably two, suitable to seal the ends of the gantry 30 and the ends of the mobile arched modules 35c and 35d when the system is in the closed configuration.

The compensation member 70 is suitable to rotate the source 31 and the detector 32 about an axis substantially parallel to the main direction (or axis of extension) 20a and, about the main axis of expansion 30a when the gantry 30 is at least in the first rotational blocked position or in the third rotational blocked position. In one embodiment, the amplitude of the additional rotation is such that the amplitude of rotation defined by the internal movers 33 and 34 plus the amplitude of the additional rotation defined by the member 70 allows the source 31 and the detector 32 to realize at least one complete rotation around the main axis of expansion 30a, the bed 20 and, therefore, around the patient. The sum of the rotations is at least equal to 360° and, preferably, substantially equal to 360°.

In one embodiment, the amplitude of the additional rotation is equal to an angle between about 100° and about 220°, or between about 145° and about 200°, or substantially equal to about 180°.

The compensating member 70 may include at least one rack 71 having a trajectory extending substantially in the shape of an arc of a circumference having its center on the main axis of expansion 30a. Also, the compensating member 70 may include at least one motorized toothed wheel or other similar device suitable to engage with the rack 71 to control the rotation of the gantry 30.

In one embodiment, the motorized toothed wheel is connected to the mobile plate 52, whereas the rack 71 is obtained on the external surface of the casing 35 and, on the external surface of the fixed arched module 35a that is on the surface facing the rotation mechanism 50.

By way of example only, each cover block 80 includes a protection 81 having a plate, a slat system, or other element suitable to overlap a section of the fixed module 35a. It has been contemplated that a motor, not shown in the drawings, suitable to move the protection 81 with respect to the ends of the mobile arched modules 35c and 35d and, thus, of the gantry 30, may also be present. In this embodiment, the motor is an electric motor and moves the protection 81 by means of a rotational movement with respect to an axis substantially perpendicular to the positioning plane 30c of the circular trajectory of expansion 30b.

In one embodiment, the motor is suitable to overlap the protection 81 with the ends of the gantry 30, closing the gantry 30 when the system is in the rest configuration or in a working configuration characterized by an extension of the gantry 30 substantially less than 360°. The motor also distances the protection 81 from the ends of the gantry 30 in order to permit the correct expansion of at least the gantry 30, when the system 1 is in the working configuration and the gantry is substantially closed, that is, when it defines a closed ring and, consequently, has an extension equal to 360° (above defined configuration of maximum extension or supplementary working configuration of maximum extension).

By way of example only, and not by way of limitation, a method of using the radiological imaging system will be described. In one embodiment, the radiological imaging system 1 is initially in the rest configuration (FIGS. 1a and 2a) with the gantry 30 arranged inside the free chamber 40a and, thus, the support surface 20b practically completely free and substantially accessible from any point.

In this embodiment, in the rest configuration the gantry 30 has the casing 35 with the mobile arched modules 35c and 35d substantially housed inside the fixed arched module 35a and the movers 33 and 34 overlapped to the fixed module 35a or, if provided, in the contracted condition.

Figure 2A:
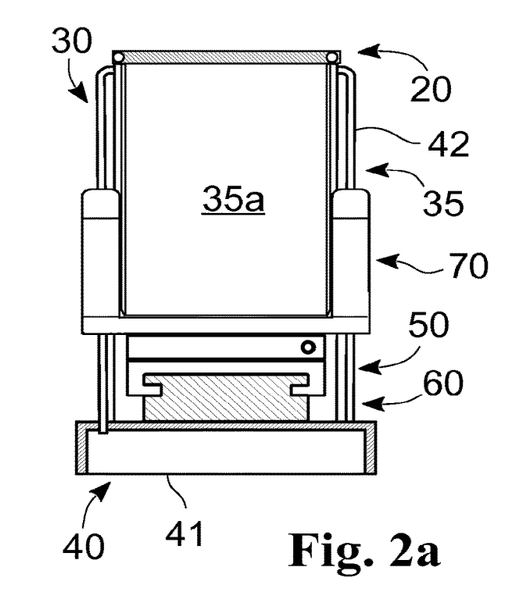
FIGS. 2a-2c are front views of part of the operating sequence of FIGS. 1a-1e.
Figure 2B:
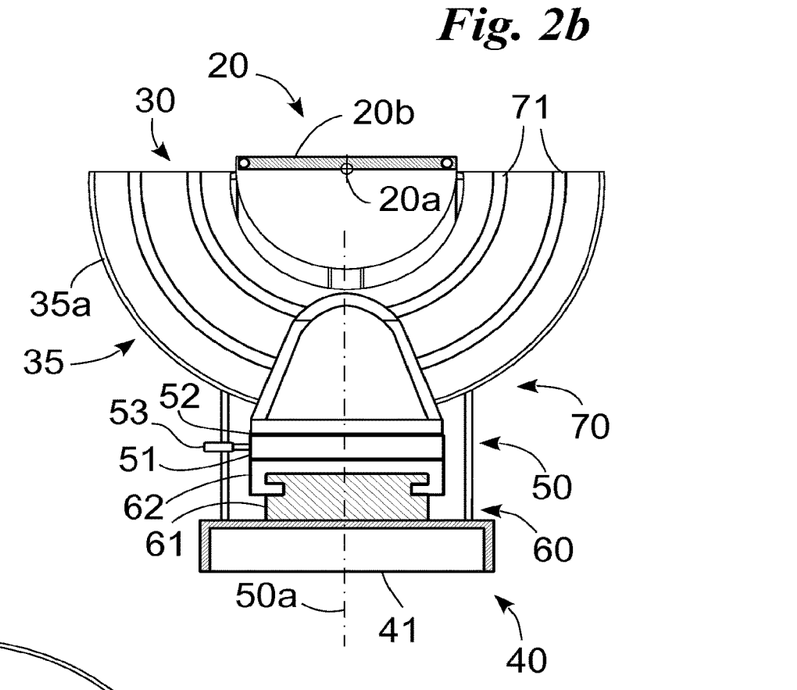
Figure 2C:
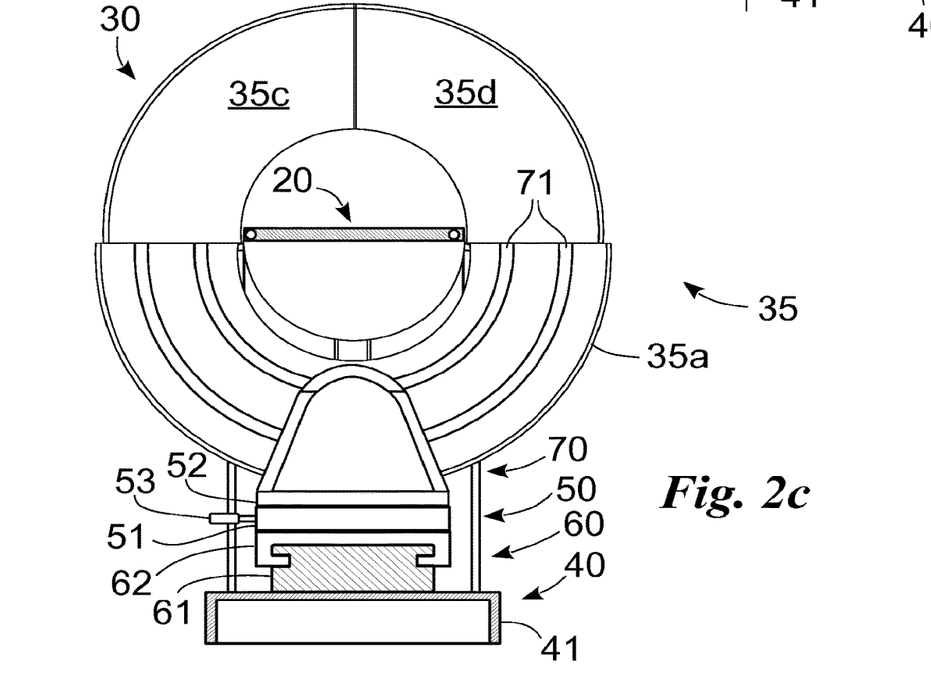

The operator places the patient on the bed 20 and controls the movement into the desired working configuration (FIGS. 1d and 2c).

In one embodiment, the operator, using the rotation mechanism 50, rotates the gantry 30 by approximately 90° to arrange the positioning plane 30c substantially perpendicular to the main direction (or axis of extension) 20a. Next, the casing 35 and the gantry 30, translate along the circular trajectory of expansion 30b until assuming the desired angular extension.

In one embodiment, should the gantry 30 become substantially closed and, thus, assume an extension of approximately 360°, each cover block 80 moves the protection 81 freeing the ends of the mobile modules 35c and 35d and of the gantry 30.

In this embodiment, during this change of configuration, the two mobile arched modules 35c and 35d rotate along the circular trajectory of expansion 30b, with opposite directions of rotation, placing the arched guides 33b and 34b on opposite sides with respect to the axis prevalent 30a (FIG. 3b).

When the desired working configuration is reached, the operator may then select the portion of the body to be analysed. In one embodiment the control unit 1a instructs each of the inner and outer carts 33c and 34c to slide along the respective arched guide 33b and 34b placing the detector 32 and/or the source 31 in the desired position. Alternatively, the movement of the inner cart 33c and/or out cart 34c and, therefore, of the detector 32 and/or the source 31 are defined, in addition to the motion of the carts 33c and 34c on the respective guide, by the control group above described.

If the movement of the cart 33c and 34c is not sufficient to reach the required position and, therefore, to allow the angular position of the source 31 and/or the detector 32 to be those optimal for the type of imaging to be performed, the control unit 1a may then activate the compensation member 70 in order to rotate the gantry 30, thus bringing the source 31 and/or the detector 32 in the proper position.

Now in this embodiment, either automatically or in response to a command given by the operator through the control unit 1a, the source 31 and the detector 32 perform the desired radiological imaging.

For example, should the operator wish to carry out a tomography and/or fluoroscopy, the radiological imaging system 1 is made to pass into the first active configuration.

As a result, the motor 32f rotates the sensors 32a and 32c, in relation to the axis of rotation 32g, in such a way that the first sensitive surface 32c is positioned substantially perpendicular to the axis of propagation 31a and in such a position as to be hit by the radiation emitted by the source 31.

After concluding the foregoing operations, the source 31 and the detector 32 perform, either automatically or in response to a command from the operator control using the control station 30, the radiological imaging procedure while the translation mechanism 60 moves the gantry 30 along the axis of translation 60a to permit the system 1 to perform radiological imaging over the entire portion to be analyzed.

Should the operator wish to use the second sensor 32c and thereby perform a different radiological imaging procedure, the operator would then control the movement into the second active configuration.

As a result, the motor 32f rotates the sensors 32a and 32c, in relation to the axis of rotation 32g, in such a way that the first sensitive surface 32b moves away from the position previously adopted. Moreover, the rotation positions the second sensor 32c in such a way second sensitive surface 32d, which is positioned substantially perpendicular to the axis of propagation 31a and in such a position as to be hit by the radiation emitted by the source 31 and to be at the same distance as that assumed by the first surface 32b in relation to the source 31 in the previous configuration.

In certain embodiments, if a 360° imaging is required, the internal movers 33 and 34 and the member 70, during the imaging, rotate the source 31 and the detector 32 in order to allow the 360° imaging.

When the radiological imaging procedure is complete, the operator may control the return of the system 1 to the rest configuration and may then, for example, perform surgery on the patient without removing the patient from the device.

Alternatively, if a second radiological imaging procedure is necessary, for example involving a translation of the detector 32 in the opposite direction, the operator controls the passage of the system 1 first into the rest configuration and then into the supplementary working configuration and then performs the second imaging procedure.

In view of the foregoing, it can be appreciated that the radiological imaging system 1, by virtue of varying both the extension of the gantry 30 and its position in relation to the bed 20, makes it possible to perform a plurality of operations/analyses on the patient without moving him from the bed 20.

In one embodiment, in the rest configuration, the gantry 30 is practically entirely housed in the free chamber 40a, so that the space occupied by the system 1 is defined by the bed 20 and by the load-bearing structure 40 and is, therefore, substantially the same as a hospital bed, that is a bed normally used to transport the patient to other areas within the hospital or to perform an operation on the patient.

Furthermore, the reduction in the overall dimensions has been achieved by displacing the internal movers 33 and 34. Additionally, the reduction in dimensions may be obtained because the internal movers 33 and 34 constitute innovative arched telescopic guides characterized by a high expansion capacity which can, in some case, permit a rotation of the body 33b and 34b, and thus, of the source 31 or detector 32 with an amplitude substantially twice that of the amplitude of the input motion of the guide 33 and 34.

Additionally, the system 1, the dimensions of which, in the rest configuration, are similar to those of an examination bed, can easily be maneuvered inside a structure/hospital.

Unlike with the known imaging devices, the radiological imaging system 1 is able to easily and readily pass through doors, in lifts or other openings normally present in a hospital.

Moreover, image acquisition by the imaging system 1 is versatile. By virtue of the internal movers 33 and 34 and the compensating member 70, the source 31 and the detector 32 can rotate by 360° so that the angle of inclination of the radiation, that is, the central axis 31a, with respect to the patient, can be adjusted as required.

Image acquisition by the imaging system 1 is also versatile by virtue of the rotation mechanism 50 which, by defining the second and the third rotational blocked position for the gantry 30 and, thus, two working configurations for the system 1, allows the detector 32 and the linear sensor (in one example), to be used in two different image acquisition directions, although other types of sensors can be employed instead.

Contrary to the known devices, where images can only be acquired with the gantry translating in a single direction, with the system 1, the gantry 30 can be rotated by about 180° so that scans can be performed in both directions and, thus, specific radiological imaging can be performed without having to move the patient.

Furthermore, by virtue of the cover blocks 80, which seal the ends of the gantry 30 when the system 1 is in the rest configuration, the entry of any blood, debris or other material that could damage the internal components of the gantry 30 can be prevented.

Consequently, an innovative radiological imaging procedure is provided by virtue of the radiological imaging system 1.

With the radiological imaging procedure, the analysis is only performed when the patient is in the ideal condition, thus limiting exposure to radiation and the costs of the analysis.

In the case of injecting a contrast liquid, the radiological imaging procedure allows the analysis to be performed when the liquid is in the portion of the body to be analyzed, thus avoiding the risk of a poor quality analysis due to the absence of the liquid in the portion to be analyzed.

In at least some cases when the correct position of the patient is essential, by being able to check the position of the portion to be analyzed before performing the radiological imaging procedure, the radiological imaging procedure is only performed when the patient is in the desired position.

Additionally, by virtue of the radiological imaging device, the procedure can be carried out without moving the patient during the entire procedure.

Modifications and variations may be made to the invention described herein without departing from the scope of the inventive concept. All the elements as described and claimed herein may be replaced with equivalent elements and the scope of the invention includes all other details, materials, shapes and dimensions.

For example, the source 31 and the detector 32 are integrally constrained to the gantry 30, which in one embodiment is free of handlers 33 and 34. In one example, the source 31 is integral with the fixed arched module 35a or one of the mobile modules 35c and 35d; and the detector 32 can be rigidly integrally with one of mobile modules 35c and 35d or to the fixed module 35a so as to be arranged on the opposite side to the spring 31 in one of the active configurations.

In one embodiment, the compensating member 70 defines an amplitude of the additional rotation substantially equal to an angle substantially greater than 180° and, in another embodiment, at least substantially 360°.

The compensating member 70, therefore, in addition to the rack 71 and the at least a motorized toothed wheel, presents an additional rack having a development trajectory substantially arc of circumference centered on the axis 30a prevalent development.

In detail, to allow the closure of the mobile arched modules 35c and 35d, the additional rack can have a different radius respect to the rack 71 and, therefore, the compensating member 70 may provide a supplementary motorized toothed wheel able to engage the additional rack commanding the rotation of the gantry 30.

One of ordinary skill in the art will appreciate that not all radiological imaging systems have all these components and may have other components in addition to, or in lieu of, those components mentioned here. Furthermore, while these components are viewed and described separately, various components may be integrated into a single unit in some embodiments.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A radiological imaging system, comprising:
   a bed extending along a main direction;
   a load-bearing structure suitable to support the bed in a raised position defining a free chamber between the load-bearing structure and the bed;
   an expandable gantry having a circular trajectory of expansion defining a positioning plane, the expandable gantry includes a source configured to emit a radiation and a detector configured to receive the radiation, and the expandable gantry having a rest configuration in which the positioning plane of the expandable gantry is substantially parallel to the main direction and the expandable gantry is at least partially housed in the free chamber.

2. The radiological imaging system of claim 1, wherein the expandable gantry includes a first working configuration wherein the positioning plane of the expandable gantry is substantially perpendicular to the main direction.

3. The radiological imaging system of claim 1, further comprising a rotation mechanism connected to the expandable gantry to rotate the expandable gantry in relation to the bed and to the load-bearing structure to vary the inclination of the positioning plane in relation to the main direction.

4. The radiological imaging system of claim 1, wherein the expandable gantry includes a casing housing the source and the detector, the casing having a fixed arched module and a first mobile arched module.

5. The radiological imaging system of claim 4, further comprising a kinematic expansion mechanism connected to the casing of the expandable gantry, the kinematic expansion mechanism translates the first mobile arched module along the circular trajectory of expansion.

6. The radiological imaging system of claim 5, wherein the casing includes the first mobile arched module disposed in a first end of the fixed arched module and a second mobile arched module disposed in a second end of the fixed arched module.

7. The radiological imaging system of claim 6, wherein the expandable gantry includes a working configuration wherein the positioning plane of the expandable gantry is perpendicular to the main direction and the ends of the first and second mobile arched modules reach a mutual contact point, and angle of extension of the casing and the expandable gantry is 360°.

8. The radiological imaging system of the claim 6, wherein the first and second mobile arched modules have an angular extension equal to about 90°, and wherein the fixed arched module has an angular extension between about 180.degree. and about 210°.

9. The radiological imaging system of claim 6, wherein the kinematic expansion mechanism is configured to move the first and second mobile arched modules in opposite directions.

10. The radiological imaging system of claim 4, wherein the first mobile arched module is substantially overlapped with the fixed arched module in the rest configuration.

* * * * *